United States Patent [19]
Cybulski

[11] Patent Number: 5,766,872
[45] Date of Patent: Jun. 16, 1998

[54] METHOD FOR ELIMINATING HEMOLYSIS INTERFERENCE IN AN AMYLASE ANALYSIS

[75] Inventor: Raymond Leon Cybulski, Elkton, Md.

[73] Assignee: Dade International Inc., Deerfield, Ill.

[21] Appl. No.: 562,547

[22] Filed: Nov. 20, 1995

[51] Int. Cl.$^6$ ................................................. C12Q 1/40
[52] U.S. Cl. .................................... 435/22; 435/210
[58] Field of Search ............................ 435/22, 210

[56] References Cited

U.S. PATENT DOCUMENTS

| | | | |
|---|---|---|---|
| 4,102,747 | 7/1978 | Driscoll et al. | 195/103.5 |
| 4,145,527 | 3/1979 | Burns et al. | 536/4 |
| 4,233,403 | 11/1980 | Menson et al. | 435/22 |
| 4,698,300 | 10/1987 | Henkel et al. | 435/18 |
| 4,963,479 | 10/1990 | Chavez et al. | 435/22 |

FOREIGN PATENT DOCUMENTS 0 510 620 A1  4/1992  European Pat. Off. .

OTHER PUBLICATIONS

Jansen & Wydeveld, Alpha–(p–Nitrophenyl)Maltoside as a Substrate for the Assay of Amylase, *Nature*, 182, 525–526, Aug. 23, 1958.

*Primary Examiner*—James O. Wilson
*Attorney, Agent, or Firm*—Cynthia G. Tymeson

[57] ABSTRACT

A method for increasing the accuracy of photometric-based assays for α-amylase by subjecting a sample to a secondary interrogating beam of radiation at a wavelength distinguishable from a primary interrogating beam of radiation. The secondary interrogating beam of radiation is indicative of an interfering reaction occurring in the absence of analyte at the primary wavelength. The secondary wavelength is outside the absorption spectrum of the analyte of interest. This secondary radiation beam's absorption is proportional to the interfering reaction at the primary wavelength.

4 Claims, No Drawings

5,766,872

METHOD FOR ELIMINATING HEMOLYSIS INTERFERENCE IN AN AMYLASE ANALYSIS

BACKGROUND OF THE INVENTION

1. Field of the Invention

The present invention relates to photometric measurements useful in homogeneous medical diagnostic assays performed on an automatic chemical analyzer. More particularly, the invention pertains to the use of photometric reaction rate measurements made at a second wavelength to correct for the effect of non-specific reactions which interfere with reaction rate measurements made at a first wavelength of interest during an analysis for α-amylase.

2. Description of the Related Art

Amylases are a group of hydrolases that split complex carbohydrates constituted of α-D-glucose units linked through carbon atoms 1 and 4 located on adjacent glucose residues. Animal amylases, including those present in humans, are α-amylases and can attack α-1 -4 linkages in a random manner anywhere along the polyglucan chain. Qualitative kinetic determinations of α-amylase (n1,4-glucan-4-glucanohydrolase) activity in human serum and urine are helpful in diagnosis of diseases of the pancreas and in investigations of the pancreatic function. The diagnosis of acute pancreatitis is sometimes difficult since a distinction must be made from other acute intra-abdominal disorders with similar findings, such as perforated gastric or duodenal ulcer, intestinal obstruction, and mesenteric vascular obstruction. In addition, most common anticoagulants inhibit amylase activity because they chelate Ca(II); furthermore, citrate, EDTA and oxalate inhibit it by as much as 15%. As a consequence, amylase assays must be performed only on serum or heparinized plasma, however both of these may be imperfectly separated and other endogenous materials, such as red blood cells, may be present causing an inaccurate assay.

Historical assay techniques were based on a change in the absorption maxima of a complex between starch and iodine as the α-amylase degraded the starch or on a measurement of the increase in reducing groups as the starch was hydrolyzed by the α-amylase. These methods are not as reliable and easy to quantitate as spectro-photometric methods using a defined substrate. A defined substrate, such as maltotetraose, is degraded by α-amylase to produce glucose which is then measured in a coupled enzyme assay. Although accurate, such methods also necessitate the complete removal of any endogenous glucose which can give an erroneous background reading within the assay.

Synthetic substrates comprising nitro aromatic glycosides have been employed in α-amylase determinations, such as reported in U.S. Pat. No. 4,145,527. The α-amylase acts preferentially on the endo bonds to form smaller fragments and therefore in order to get complete action to generate the chromophore, e.g. nitrophenol, an additional supporting enzyme must be employed. The use of aromatic glycosides directly without the use of an additional supporting enzyme has generally proved to be impractical because of poor kinetics and/or poor rate of color release. One such assay involving a synthetic substrate has been described (*Nature*, 182 (1958) 525–526) in which a p-nitrophenol derivative of maltose is used. The p-nitrophenol replaces the anomeric hydroxyl group of maltose. Amylase causes cleavage of the substrate to produce p-nitrophenol which can be monitored at 41 0 nm. However, the assay is 16 hours long and maltase also cleaves the substrate.

In all of the above methods, it is generally recognized that spectrophotometric methods may be adversely affected by the presence of certain endogenous materials in body fluids. Typically this interference is attributed to absorbance of the interfering substance at the wavelength of interest. In many cases a sample blank is required to correct for the interference. Another approach is the use of rate techniques which, in effect, subtract out the absorbance attributable to the interfering compound. These approaches are limited to those situations where the absorbance due to the interference does not exceed the capacity of the spectrophotometer. In response to this concern, since many materials endogenous to body fluids absorb only at lower wavelengths (<500 nm), there have been efforts to develop new substrates for enzyme determinations which absorb at wavelengths greater than 600 nm. Two such examples are disclosed in U.S. Pat. No. 4,933,277 and JP No. 2,306,990.

Absorption measurements made at secondary or reference wavelengths (typically referred to as the blanking wavelength) are routinely used in spectrophotometric determinations to correct for errors that otherwise may arise due to gross environmental differences, such as air bubbles, debris, scratched surfaces, etc. Implicit in the selection of a reference wavelengths is the assumption that the gross environmental factors have similar effects across a wide absorbance range. Thus secondary or blanking wavelengths are normally chosen to be clearly outside the spectrum of the chromophore of interest and on the upper end of the absorbance spectrum. Unfortunately, these methods of the prior art fail to account for ancillary reactions which occur as a result of the presence of certain endogenous materials in bodily fluids.

An endogenous substance may interfere with a spectrophotometric method by participating in a reaction, unrelated to the chromophore generating scheme, but which affects the absorbance of the assay matrix at the wavelength of interest. One α-amylase assay which encounters this interference reaction uses a synthetic substrate to measure activity, as described in U.S. Pat. 4,963,479. It is susceptible to such ancillary reaction interference by hemolyzed samples. The hemoglobin induces a negative bias in the absorption measurements which results in low estimates of α-amylase activity. The negative bias obtained with 500 mg/dL hemolysate in the sample matrix has been observed to vary unpredictably from less than 10 International Unit/Liter (U/L) to greater than 40 U/L. In the absence of α-amylase the hemolysis effect is observed, after the hemolyzed serum is added to the reaction mixture, as a slow decrease in 405 nm. absorbance. The mechanism for the inhibition is not known, however it may be supposed that iron in the hemoglobin is reacting with either the thiocyanate or hydrazoic acid in the reaction mixture forming a product with a lower extinction coefficient at 405 nm. The lot to lot variability suggests that the rate of formation of this product is dependent on the presence of unknown trace substances in the reagent, such as metals or an as yet unidentified substance.

SUMMARY OF THE INVENTION

The present invention addresses a problem of the prior art analysis systems using photometric analysis in homogeneous assays, wherein absorption interference is caused by a spurious rate of change in absorbance due to ancillary chemical reactions between a substance or substances endogenous to body fluids, such as hemoglobin, and a component(s) of the reaction mixture. The present invention increases the accuracy of photometric-based enzyme directed assays by subjecting the reaction vessel to a secondary interrogating beam of radiation selected to have a wavelength distinguishable from a primary interrogating beam of radiation that has radiation absorption peak(s) peculiar to the chromophore of interest. The wavelength of the secondary interrogating beam of radiation is selected (1) to be out of the radiation absorbance peak(s) of the chromophore of interest, and (2) to provide a rate of absorbance change equal to or proportional to that absorbance rate observed in the absence of analyte at the primary wavelength.

The assay reaction mixture, including the α-amylase and a chromogenic substrate, is subjected to a first or primary wavelength related to the primary reaction between α-amylase and the chromogenic substrate and the absorbance measured. Simultaneously, the assay reaction mixture is subjected to a second wavelength related only to the absorbance interference caused by the reaction of an endogenous substance with component(s) of the reaction mixture, and the absorbance measured. The rates of change in absorbance are substracted. This method thereby minimizes the effect of endogenous materials interfering with photometric determinations through unforeseen reactions that induce a spurious rate of change in the absorbance of the assay mixture.

DETAILED DESCRIPTION OF THE PREFERRED EMBODIMENTS

It is a common practice of the prior art to make spectrophotometric measurements at a single wavelength distinguishable from the primary interrogating beam of radiation so as to account for vagarite in the composition of the vessel 24 and/or spectral changes due to oddities in the reagent mixture, e.g. air bubbles, debris, etc. However, as mentioned previously, spectrophotometric measurements at a single wavelength do not correct for interference in homogeneous assays caused by an undesirable rate of change in absorbance due to unknown chemical reactions between a substance or substances endogenous to bodily fluids, such as hemolysis, and components of the reaction mixture, especially when such rates vary from one reagent lot to another.

The present invention provides a method for increasing the accuracy of photometric-based assays by subjecting a uniform matrix (the assay reaction mixture) including α-amylase in a test sample, an interfering endogenous substance, and a chromogenic substrate for the α-amylase to a primary wavelength and to a second wavelength, measuring the rates of change in absorbance of the test sample matrix at each wavelength, and subtracting the rate of change in absorbance at the second wavelength from the rate of change in absorbance at the first wavelength. The secondary wavelength is selected to not be included within the absorption peak(s) of the chromophore of interest. The absorbance at the secondary wavelength also has a rate of change equal to or proportional to that observed in the absence of analyte at the primary wavelength. While it is known that endogenous materials may interfere with photometric determinations through unforeseen reactions that induce an undesirable rate of absorbance change within the assay mixture; the present invention corrects for the undesirable rate of change by subtracting the absorbance values, or a proportion thereof, preferably from 60 to 100 percent, most perferably 90 to 100 percent, of the assay mixture at a wavelength distinguishable from the primary interrogating beam of radiation. A key feature of this invention is that the interfering reaction must produce a change in the absorbance of the solution at a secondary wavelength which is outside the absorption spectrum of the component of interest. This change should be equal to or proportional to the absorbance change that is causing the interference at the primary wavelength.

As shown below in Formula 1,the α-amylase assay involves the use of a chromogenic substrate preferably 2-chloro-4-nitrophenol linked with maltotriose in a fluid matrix. Other substrates which produce matrixes having a secondary reaction characterized by absorption outside the primary reaction's absorbance bandwidth are also contemplated within the bounds of the present invention. The direct reaction of α-amylase with the substrate results in the formation of 2-chloro-4-nitrophenol, which is monitored spectrophotometrically. The α-amylase hydrolyzes the 2-chloro-4-nitrophenyl-α-D-maltotrioside (CNPG3) to release 2-chloro-4-nitrophenol (CNP) and form 2-chloro-4-20 nitrophenyl-α-D-maltoside (CNPG2), maltotriose (G3) and glucose (G).

The rate of formation of the CNP can be detected spectrophotometrically at 405 nm (the primary wavelength) to give a direct measurement of α-amylase activity in the sample. The reaction proceeds rapidly, and can be easily automated. No coupling enzymes are required however, the reaction has been observed to be inhibited by endogenous factors.

Formula 1

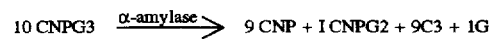

Based on the absorption spectra of CNP which peaks at 405 nm and drops to a low level at 500 nm, conventional "blanking" techniques practiced in the art would recommend a reference wavelength of 510 nm for the aforedescribed assay. As such and as discussed hereinbefore, the assay would inaccurately account for the α-amylase concentration in hemolyzed samples. In addition, lot-to-lot variations in the amylase content of individual samples are observed. According to this invention the second or "blanking" wavelength is selected to be 577 nm. It can actually fall in the range of about 565 nm to 585 nm. At this wavelength, all of the inhibiting effect of endogenous factors are experienced, the same as at 405 nm, and yet at this wavelength the method is essentially non-responsive to α-amylase.

Table 1 shows a comparison of the results obtained when hemolysate spiked samples, lot GB5192,lot CD5084 and lot D50029, are assayed with three different lots of AMY Flex™ reagent cartridges (DF17A) using 510 nm as a blanking wavelength and using 577 nm as an ancillary reaction rate measurement. When performed according to the method of the present invention, accounting for the 577 nm ancillary reaction rate measurement significantly improves the accuracy of and the lot to lot consistency of the α-amylase measurements.

TABLE 1

| Hemolysate | 510 nm | | | 577 nm | | |
|---|---|---|---|---|---|---|
| mg/dL | GB5192 | CD5084 | D50029 | GB5192 | CD5084 | D50029 |
| 0 | 50 | 50 | 50 | 50 | 50 | 50 |
| 100 | 44 | 47 | 43 | 48 | 48 | 47 |
| 200 | 42 | 46 | 40 | 48 | 49 | 47 |
| 300 | 38 | 45 | 38 | 46 | 49 | 46 |
| 400 | 37 | 44 | 36 | 47 | 49 | 46 |
| 500 | 34 | 42 | 34 | 46 | 48 | 46 |

EXAMPLE

Enzymatic spectrophotometric assay for α-amylase with 2-chloro-4-nitrophenyl-α-D-maltotrioside The reagent CNPG3 is available commercially under the tradename AMY Flex™ reagent cartridge (DF17A) which is intended for the detection of α-amylase in human specimens using the DuPont DIMENSION® Clinical Chemistry System.

The assay protocol for α-amylase involves the use of 2-chloro-4-nitrophenyl-α-D-maltotrioside reagent, hereafter designated CNPG3, being a solution of 2.25 millimoles/L 2-chloro-4-nitrophenyl-α-D-maltotrioside in 0.5 molar 2-N-(morpholino)-ethanesulfonic acid (MES) buffer, pH =6.0, containing 350 millimoles/L of sodium chloride, 6 millimoles/L of calcium acetate and 900 mM thiocyanate and/or 0.1 % azide.

The following procedural method can be used to perform an α-amylase assay using the apparatus of this invention in the DuPont DIMENSION® Clinical Chemistry system.
Procedure 1. Prior to testing specimens containing unknown concentrations of α-amylase, three verifier samples are normally tested in a "Verification" mode of the system. The "assigned values" of each verifier are manually entered into the Dimension® computer and appropriate verifiers and reagent cartridge are loaded on the system. After the tests are completed, the computer automatically performs a mathematical regression using the signals and assigned-values of all three verifiers. A verification slope between 0.90 to 1.10 indicates that the system is performing properly. 2. An amylase test is scheduled on computer. A sample specimen is placed in a sample well and the AMY Flex™ reagent cartridge is loaded onto sample transport means. The sequence of events by which the system performs the α-amylase test follow. 3. Upon receiving commands to perform an α-amylase test, the system forms a reaction vessel situated around the perimeter of the sample transport means. 4. A 220 uL aliquot of CNPG3 is automatically withdrawn from the AMY Flex™ reagent cartridge and dispensed, followed by 130 uL water, into the reaction vessel and mixed. 5. After 60 to 102 seconds, a 14 uL sample of the specimen is withdrawn from the sample well and dispensed, followed by 36 uL water, into the reaction vessel and mixed to provide a uniform matrix comprising the specimen and CNPG3 by thoroughly mixing the specimen with the CNPG3 solution. 6. After approximately 72 seconds, the absorbance at ten wavelengths are measured. The difference of absorbance between 405 nm and 577 nm is computed and recorded as rA.

The exact time of the first reading is recorded and designated r1. 7. Approximately 144 seconds after the initial reading, the absorbance of reaction vessel 23 at 10 wavelengths is measured again. The difference of absorbance between 405 nm and 577 nm is computed and recorded as rB. The exact time of the second reading is recorded and designated r2. 8. The rate of absorbance change is calculated as $\Delta mA/min$.

$$\Delta mA/min = (rB-rA)/(r2-r1).$$

The α-amylase activity of each sample and control is known to be determinable using the following formula:

$$\alpha\text{-amylase (U/L)} = 5.4 * \Delta mA/min.$$

Where:

$\Delta A/min.$ =Change in milli absorbance units per minute for the sample or control, and 5.4 =Conversion factor.

What is claimed is:

1. A method for assaying the amount of α-amylase in a test sample having α-amylase and possibly an interfering endogenous substance, the method comprising:

adding a chromogenic substrate to the test sample to provide a uniform solution, measuring the rate of change in absorbance of the test sample matrix at a first wavelength related to a primary reaction between α-amylase and the chromogenic substrate, and measuring the rate of change in absorbance of the test sample matrix at a second wavelength related to an absorbance interference caused by the reaction of any endogenous substance with a component or components of the uniform solution wherein the second wavelength is selected such that the absorption rate in the absence of α-amylase is proportional to that absorption rate of change observed at the first wavelength and wherein the second wavelength is outside the range of wavelength related to the primary reaction between α-amylase and the chromogenic substrate, and subtracting the rate of change in absorbance determined at the second wavelength from the rate of change of absorbance determined at the first wavelength, thereby to correct for the effects of any interfering endogenous substance.

2. The method of claim 1 wherein the chromogenic substrate is 2-chloro-4-nitrophenol linked with maltotriose.

3. The method of claim 2 wherein the first wavelength is in the range 390 to 420 nm.

4. The method of claim 2 wherein the second wavelength is in the range 565 to 585 nm.

* * * * *

UNITED STATES PATENT AND TRADEMARK OFFICE
CERTIFICATE OF CORRECTION

PATENT NO. : 5,766,872
DATED : June 16, 1998
INVENTOR(S) : Raymond Leon Cybulski It is certified that error appears in the above-identified patent and that said Letters Patent is hereby corrected as shown below:

Column 4, Line 16: Delete "20"

Column 6, Line 38: Delete "wavelength" and insert --wavelengths--.

Signed and Sealed this

Twenty-second Day of September, 1998

Attest:

BRUCE LEHMAN

*Attesting Officer*  *Commissioner of Patents and Trademarks*